United States Patent
Castle et al.

[11] Patent Number: 6,024,689
[45] Date of Patent: Feb. 15, 2000

[54] WEDGE FOR SHAPING A RADIATION DOSE TO THE HEAD

[76] Inventors: Steven K.B. Castle, 67 Council Rock Ave., Rochester, N.Y. 14610; Kurt N. Laurer, 231 Seneca Pkwy., Rochester, N.Y. 14613

[21] Appl. No.: 08/617,257

[22] Filed: Mar. 18, 1996

[51] Int. Cl.⁷ ........................................ A61N 5/00

[52] U.S. Cl. .................................................. 600/1

[58] Field of Search ........................ 600/1–8; 128/897–98

[56] References Cited

FOREIGN PATENT DOCUMENTS

| | | | |
|---|---|---|---|
| 2672220 | 8/1992 | France | 600/1 |
| 4223488 | 1/1994 | Germany | 600/1 |
| 4023663 | 10/1994 | WIPO | 600/1 |
| 5000204 | 1/1995 | WIPO | 600/1 |

*Primary Examiner*—John P. Lacyk

[57] ABSTRACT

A three dimensional radiation therapy treatment device, has a heel on three sides forming a half crater shape, for the purpose of shaping a beam of radiation more accurately to a persons head. The wedge is constructed of a radiation attenuating material with the dimensions determined by the treatment machine utilized.

2 Claims, 5 Drawing Sheets

C-L Wedge Shown In Relation To Human Head

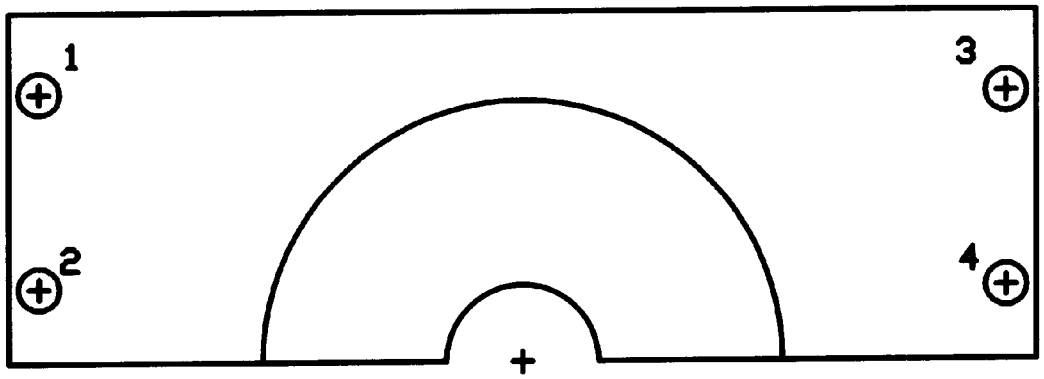
Figure 1. Top View Showing The C-L Wedge Mounting Hole Arrangement For Use With A Base Plate (Optional)

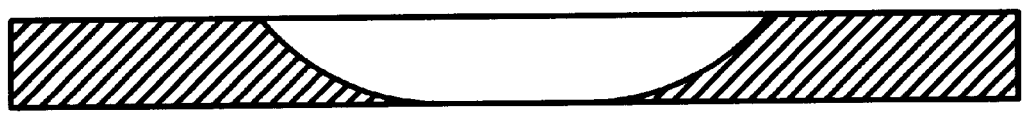
Figure 2. Front View of C-L Wedge

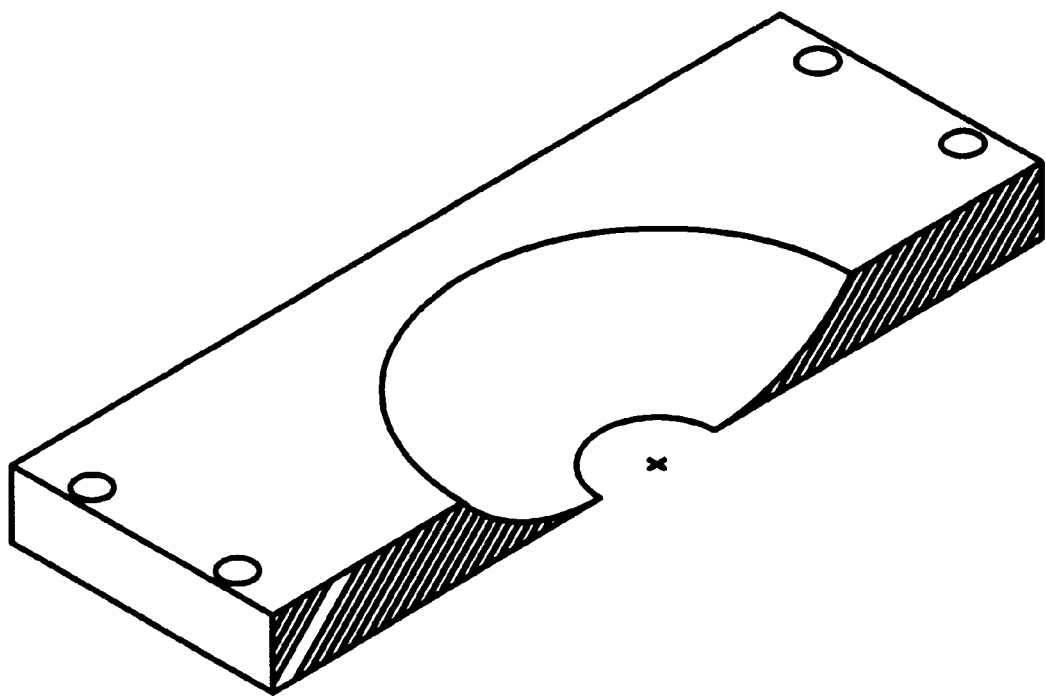
Figure 3. Isometric View of C-L Wedge

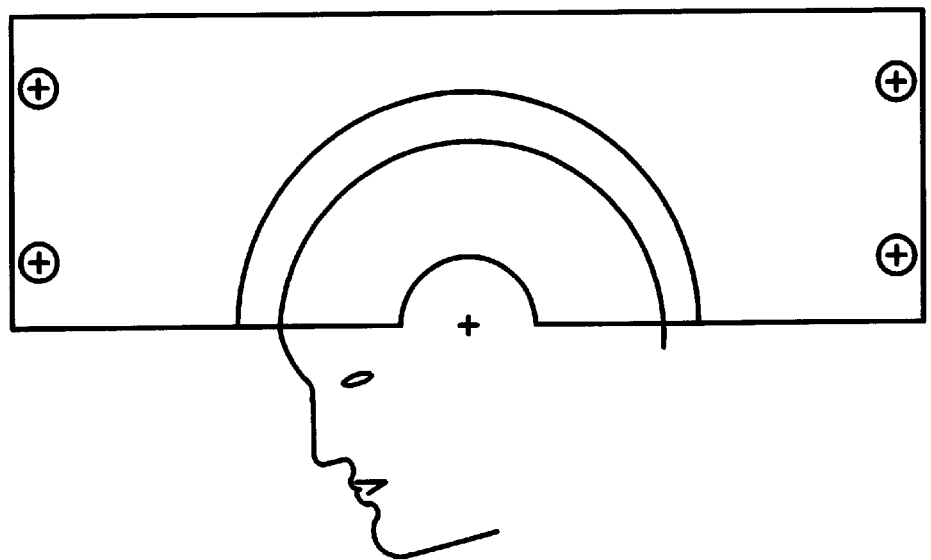
Figure 4. C-L Wedge Shown In Relation To Human Head

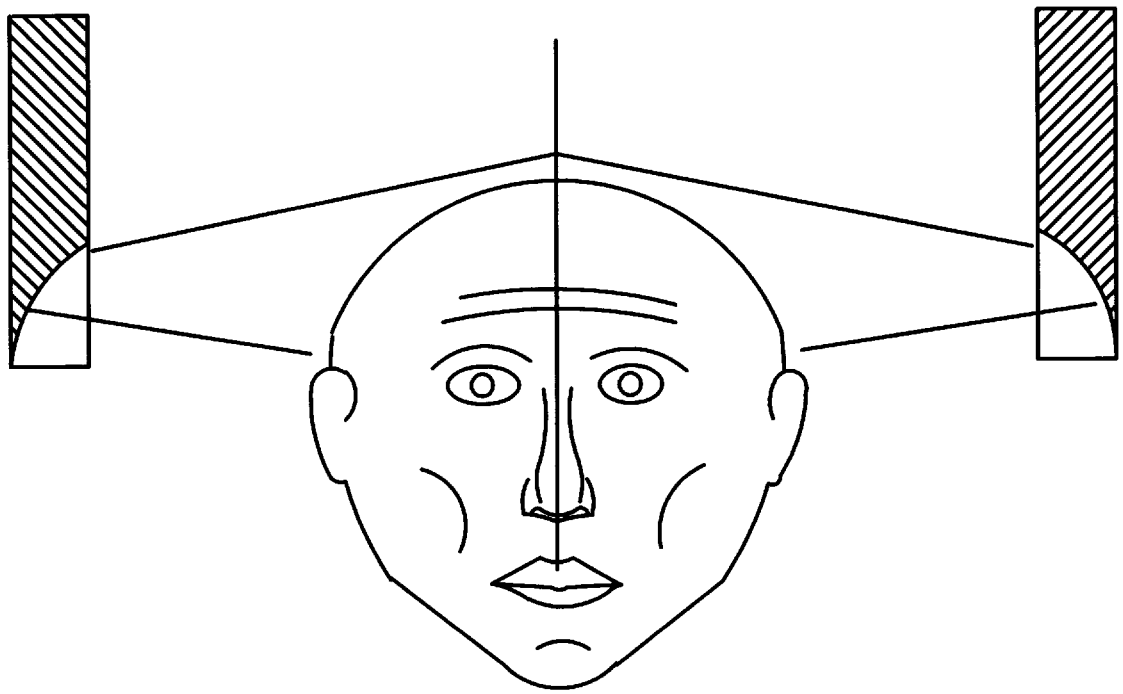
Figure 5. View Of C-L Wedge In Relation to A Human Head.

WEDGE FOR SHAPING A RADIATION DOSE TO THE HEAD

BACKGROUND OF THE INVENTION

1. Field of Invention

The invention relates to an improved design of an accessory wedge used in the medical field of Radiation Therapy.

2. Description of the Prior Art

Wedges are radiation therapy treatment accessories used to attenuate the shape a radiation beam. The purpose is to better distribute the isodose lines of radiation to prevent against 'cold' or 'hot' spots of variable doses. Currently, wedges are two dimensional. This design features one slope and one heel. This limits the use of a wedge to anatomical structures with one corresponding slope.

Radiation treatments to the brain are a common occurrence. The standard setup is to treat the whole brain. This creates a problem due to the sloping of the head; similar to that of a ball cut in half. One side is long, straight, and thick; while the remainder is arced and sloping. Since the current wedge does not conform to this shape, wedges are not utilized. The result is a 'hot' spot is created along the outer ring. This 'hot' spot leaves a strong burn to the patient's skin along this thinner outer ring. This limits the tolerable dose which may be applied. Also, this portion of the brain contains the cerebrum and gray matter. Memory, thinking and reasoning are three functions controlled in this region which directly effect the quality of life. This area cannot afford to be compromised with high amounts of radiation which 'hot' spots would create. Because there is currently no way of delivering a more balanced dose a passive treatment for an aggressive disease is done. The prognosis for the patient is usually poor.

SUMMARY OF THE INVENTION

The invention is an improved design of a radiation therapy treatment accessory known as a wedge. This treatment accessary is three dimensional, creating a half crater shape, which is designed for the application of one specific area: the brain.

It is an object of the invention to provide a higher quality therapeutic treatment to cancer patients receiving radiation therapy treatment to the brain.

BRIEF DESCRIPTION OF THE DRAWINGS

FIG. 1 Top view of a Wedge in accordance with the invention, the dimensions describe.

FIG. 2 Side view of the Wedge.

FIG. 3 Three dimensional view of the Wedge.

FIG. 4 is a diagrammatic view of the invention showing the Wedge and its position in relation to the patient. This demonstrates the quarter sperical depression of the wedge and its relation to the roundness of the person's head.

FIG. 5 is a diagrammatic view of the invention showing the position of the wedge in relation to the treatment machine and the persons head.

DESCRIPTION OF THE PREFERRED EMBODIMENT

Referring to FIGS. 1, 2, & 3 an embodiment of the Wedge 10 is shown. In this embodiment, the design of the Wedge is outlined. The Wedge is formed of a body 12 of radiation attenuating dense material. The design features a half crater shape 14 as illustrated in the sectional diagram (FIG. 2). The dimensions are selected to conform with an average person's head size and the type of therapeutic treatment machine utilized.

Referring to FIGS. 4 & 5, an example of the use of the wedge is illustrated. FIG. 1 shows the field of area treated with radiation on a standard whole brain treatment with the Wedge superimposes onto the treatment field. FIG. 5, demonstrates the position of the wedge 10 in relation to the patient 16 and treatment machine 18. As a beam 20 travels it diverges. The position of the wedge along this divergence varies from one treatment machine to the next. This position is important when outlining dimensions.

Each company mounts their own wedges differently. It may be, but not limited to, a carousel, plate, or slide which has a means of locking in position. This said design is engineered to allow for universal application to various treatment machines.

I claim:

1. A wedge for shaping a beam of radiation comprising:

a rigid body formed from radiation attenuating material having a half cratered surface sized so that its projection relative to a radiation source corresponds to the dimensions of a person's head, accounting for dimensional variances do to source to wedge distances and patient positions;

a means for mounting the body relative to a radiation therapy treatment machine.

2. A therapeutic means of distributing radiation three dimensionally to the head of a patient comprising the steps of positioning a rigid body formed from radiation attenuating material and having a half cratered surface; positioning the rigid body between a radiation source and a patient's head so that the projection of the half cratered surface relative to the radiation source corresponds to the size of the patient's head; and irradiating the head through the rigid body.

* * * * *